United States Patent [19]

Warnant et al.

[11] 4,151,195
[45] Apr. 24, 1979

[54] NOVEL RACEMIZATION PROCESS

[75] Inventors: Julien Warnant, Neuilly-sur-Seine; Jacques Prost-Marechal, Paris; Philippe Cosquer, St. Denis, all of France

[73] Assignee: Roussel Uclaf, Paris, France

[21] Appl. No.: 789,843

[22] Filed: Apr. 22, 1977

[30] Foreign Application Priority Data

Apr. 23, 1976 [FR] France .................. 76 12093

[51] Int. Cl.² .................................. C07C 121/75
[52] U.S. Cl. ...................................... 260/465 D
[58] Field of Search .................. 260/465 D; 560/124

[56] References Cited

U.S. PATENT DOCUMENTS

| 3,046,299 | 7/1962 | Julia | 560/124 |
| 3,786,070 | 1/1974 | Martel et al. | 560/124 |
| 3,906,026 | 9/1975 | Nagase et al. | 560/124 |

FOREIGN PATENT DOCUMENTS 2240914 3/1975 France.

Primary Examiner—Elbert L. Roberts
Assistant Examiner—Molly C. Eakin

Attorney, Agent, or Firm—Hammond & Littell

[57] ABSTRACT

A process for the preparation of an ester of chiral (A) acid with a racemic (R,S) α-cyano-3-phenoxybenzyl alcohol (B) by reacting an ester of chiral (A) acid with α-cyano-3-phenoxybenzyl alcohol of the formula

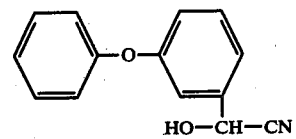

B in its optically active (R) form or (S) form or a mixture of esters of said (R) alcohol and (S) alcohol in non-equimolecular proportions with a base selected from the group consisting of ammonia, primary, secondary and tertiary amines, quaternary ammonium compounds, liquid amines of high molecular weight and a catalytic amount of a strong base in at least one solvent for the starting esters and in which the ester of racemic alcohol is soluble and recovering from the resulting solution the ester of chiral (A) acid with racemic (R,S) alcohol.

25 Claims, No Drawings

NOVEL RACEMIZATION PROCESS

STATE OF THE ART

French Pat. No. 2,240,914 describes insecticides of the pyrethrin type.

OBJECTS OF THE INVENTION

It is an object of the invention to provide a novel process for the preparation of esters of chiral (A) acid and racemic α-cyano-3-phenoxybenzyl alcohol in a simple, economical fashion.

This and other objects and advantages of the invention will become obvious from the following detailed description.

THE INVENTION

The novel process of the invention for the preparation of esters of chiral (A) acid and (R,S) α-cyano-3-phenoxybenzyl alcohol comprises reacting an ester of chiral (A) acid with α-cyano-3-phenoxybenzyl alcohol of the formula

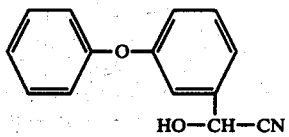

B in its optically active (R) form or (S) form or a mixture of esters of said (R) alcohol and (S) alcohol in non-equimolecular proportions with a base selected from the group consisting of ammonia, primary, secondary and tertiary amines, quaternary ammonium compounds, liquid amines of high molecular weight and a catalytic amount of a strong base in at least one solvent for the starting esters and in which the ester of racemic alcohol is soluble and recovering from the resulting solution the ester of chiral (A) acid with racemic (R,S) alcohol. This process will be called in the following process α'.

The invention also comprises a process for the preparation of an ester of chiral (A) acid and racemic (R,S) α-cyano-3-phenoxybenzyl alcohol which comprises reacting an ester of chiral (A) acid with α-cyano-3-phenoxybenzyl alcohol of the formula

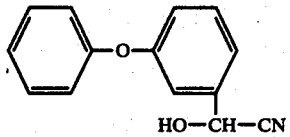

B in its optically active (R) form or (S) form or a mixture of esters of said (R) alcohol and (S) alcohol in non-equimolecular proportions with a base selected from the group consisting of ammonia, secondary and tertiary amines and a catalytic amount of a strong base in at least one solvent for the starting esters and in which the ester of racemic alcohol is soluble and recovering from the resulting solution the chiral (A) acid ester of racemic (R,S) alcohol. This process will be called process α.

The chiral acid (A) may possess an asymetric carbon atom.

Thus, the invention has as object a procedure conforming to general process α' and particularly general process α characterized in that chiral (A) acid is an acid possessing an asymetric carbon atom. Chiral (A) acid may also be an acid possessing 2 asymetric carbon atoms, particularly a cyclopropane carboxylic acid in which two of the carbon atoms of the ring are asymetric carbon atoms.

The invention has as the object a process conforming to the general process α' and notably the general process α characterized in that the chiral (A) acid is an acid possessing 2 asymetric carbon atoms and more particularly a process conforming to general process α' and particularly general process α characterized in that chiral (A) acid is a cyclopropane carboxylic acid with 2 carbon atoms of the ring being asymetrical.

The chiral (A) cyclopropane carboxylic acids which possess asymetric carbon atoms in the 1- and 3-positions are preferably optically active cyclopropane carboxylic acids of cis or trans structure of the formula

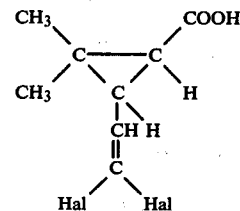

wherein Hal is chlorine or bromine. Using a simple nomenclature, the acids of 1R, 3R structure are designated as (1R, cis) acid and acids of the 1R, 3S structure are designated as (1R, trans) acids. Among the preferred chiral cyclopropane carboxylic acids are 2,2-dimethyl-3R-(2,2-dibromovinyl)-cyclopropane-1R-carboxylic acid or 1R, cis 2,2-dimethyl-3-(2,2-dibromovinyl)-cyclopropane carboxylic acid and 2,2-dimethyl-3R-(2,2-dichlorovinyl)-cyclopropane-1R-carboxylic acid or 1R, cis 2,2-dimethyl-3-(2,2-dichlorovinyl)-cyclopropane-carboxylic acid.

The basic agent used in the general process α of the invention in the presence of which is effected the transformation into the ester of the racemic alcohol is preferably selected from the group consisting of ammonium hydroxide, triethylamine, diethylamine, pyrrolidine, morpholine, piperidine and the strong bases which are used in catalytic amounts such as sodium hydroxide, potassium hydroxide, alkali metal alcoholates, alkali metal amides and alkali metal hydrides.

The basic agent used in the general process α' of the invention in which is effected the transformation into an ester of the racemic alcohol is preferably selected from the group consisting of ammonium hydroxide, n-butylamine, triethylamine, diethylamine, pyrrolidine, morpholine, piperidine, tetrabutylammonium hydroxide, Amberlite LA$_2$ and strong bases used in catalytic amounts such as sodium hydroxide, potassium hydroxide, alkali metal alcoholates, alkali metal amides and alkali metal hydrides. Amberlite LA$_2$ is a high molecular weight liquid amine sold by Rohm and Haas and equally useful as the basic agent are other liquid Amberlites such as Amberlite LA$_1$.

The above list of preferred bases for the process of the invention is not intended to be limiting. Other bases of analogous strength may be used without departing from the scope of the invention.

The solvent or mixture of solvents used in the general process α' and particularly general process α of the invention in which is effected the transformation into the esters of the racemic alcohol are preferably selected from the group consisting of ketones, monocyclic aromatic hydrocarbons, ethers oxides, dimethylformamide, dimethylsulfoxide and mixtures of the solvents and particularly preferred are the group consisting of acetone, benzene, dioxane, tetrahydrofuran, dimethylformamide, dimethylsulfoxide and mixtures of the said solvents.

For the racemization to be effected in a complete fashion, it is necessary that the starting ester or mixture of esters be soluble in the reaction medium. The esters of the alcohol of the (S) structure are generally less soluble than the esters of the alcohol of the (R) structure so that in practice, it is particularly important that the starting ester of the (S) alcohol present alone or in the mixture of starting esters is soluble in the volume of solvent (or mixture of solvents) used, at the temperature of the reaction.

The reaction temperature influences the speed of the reaction. The duration of the reaction is notably a function of the temperature as well as the nature of the base used. The list of solvents or mixtures of solvents cited above permitting total solubilization of the reaction products is not limitative and only corresponds to a preferred operating mode of the process of the invention. Other solvents or solvent mixtures assuming total solubilization of the reaction products may be used without departing from the scope of the invention.

Among the chiral (A) acids of the cyclopropane carboxylic acid type, one of the preferred acids of the invention is 2,2-dimethyl-3R-(2,2-dibromovinyl)-cyclopropane-1R-carboxylic acid or 1R, cis 2,2-dimethyl-3-(2,2-dibromovinyl)-cyclopropane-carboxylic acid.

The invention has for its object a process for the transformation according to process α characterized in that an ester of 2,2-dimethyl-3R-(2,2-dibromovinyl)-cyclopropane-1R-carboxylic acid and the optically active (R) or (S) isomer of α-cyano-3-phenoxybenzyl alcohol or a mixture of the (R) and (S) isomer in non-equimolar proportions is subjected to a basic agent selected from the group consisting of ammonium hydroxide, secondary and tertiary amines and a catalytic amount of a strong base in one or more solvents in which the starting ester is soluble and in which the ester of the racemic alcohol is soluble and from the reaction solution the ester of 2,2-dimethyl-3R-(2,2-dibromovinyl)-cyclopropane-1R-carboxylic acid and (R,S) α-cyano-3-phenoxybenzyl alcohol is isolated. This process is called the β-process.

In the said process, the basic agent is preferably selected from the group consisting of ammonium hydroxide, triethylamine, diethylamine, pyrrolidine, morpholine, piperidine and among the strong bases, sodium hydroxide, potassium hydroxide, alkali metal alcoholates, alkali metal amides and alkali metal hydrides. The solvent system is preferably selected from the group consisting of acetone, benzene, dioxane, tetrahydrofuran, dimethylformamide, dimethylsulfoxide and mixtures of the said solvents.

The invention especially has for its object a process conforming to process β for transforming (R) α-cyano-3-phenoxybenzyl 2,2-dimethyl-3R-(2,2-dibromovinyl)-cyclopropane-1R-carboxylate into (R,S) α-cyano-3-phenoxybenzyl 2,2-dimethyl-3R-(2,2-dibromovinyl)-cyclopropane-1R-carboxylate comprising reacting the starting ester of the (R) alcohol with a basic agent selected from the group consisting of ammonium hydroxide, secondary and tertiary amines and catalytic amounts of a strong base in a solvent selected from the group consisting of acetone, benzene, dioxane, tetrahydrofuran, dimethylformamide, dimethylsulfoxide and mixtures of the said solvents and isolating the ester of the racemic alcohol from the reaction solution. This process will be called process γ.

The said transformation of (R) α-cyano-3-phenoxybenzyl 2,2-dimethyl-3R-(2,2-dibromovinyl)-cyclopropane-1R-carboxylate into the ester of the (R,S) alcohol is advantageously effected in acetone in the presence of triethylamine and the ester of the (R,S) alcohol is recovered from the reaction solution by distillation to dryness.

The invention also has for its object a process according to process β for transforming a mixture of (R) α-cyano-3-phenoxybenzyl 2,2-dimethyl-3R-(2,2-dibromovinyl)-cyclopropane-1R-carboxylate and (S) α-cyano-3-phenoxybenzyl 2,2-dimethyl-3R-(2,2-dibromovinyl)-cyclopropane-1R-carboxylate in non-equimoler proportions into (R,S) α-cyano-3-phenoxybenzyl 2,2-dimethyl-3R-(2,2-dibromovinyl)-cyclopropane-1R-carboxylate comprising reacting the starting mixture of esters with a base selected from the group consisting of ammonium hydroxide, secondary and tertiary amines and a catalytic amount of a strong base in a solvent selected from the group consisting of acetone, benzene, dioxane, tetrahydrofuran, dimethylformamide, dimethylsulfoxide and mixtures of the said solvents and then isolating the ester of the racemic alcohol from the reaction solution. This process will be called process δ.

This transformation of the mixture of ester of the (R) and (S) alcohol in non-equimolecular proportions into the ester of the racemic alcohol is advantageously effected in benzene in the presence of triethylamine and recovering the ester of the racemic alcohol by distilling the reaction solution to dryness.

The invention still has for its object a process conforming to process β characterized in that the starting ester is (S) α-cyano-3-phenoxybenzyl 2,2-dimethyl-3R-(2,2-dibromovinyl)-cyclopropane-1R-carboxylate. This process will be called process ε.

The transformation of the ester of the (S) alcohol into the ester of the racemic alcohol is effected advantageously in acetone in the presence of triethylamine.

The invention still has for its object a process according to general process α' characterized in reacting an ester of 2,2-dimethyl-3R-(2,2-dibromovinyl)-cyclopropane-1R-carboxylic acid and the (R) or (S) optically active isomer of α-cyano-3-phenoxybenzyl alcohol or a non-equimolecular mixture of the (R) and (S) isomers with a base selected from the group consisting of ammonium hydroxide, primary, secondary and tertiary amines, quaternary ammonium compounds, high molecular weight liquid amines and a catalytic amount of a strong base in at least one solvent in which the starting ester is soluble and the racemic alcohol ester is soluble and then recovering from the reaction mixture the resulting racemic (R,S) α-cyano-3-phenoxybenzyl 2,2-dimethyl-3R-(2,2-dibromovinyl)-cyclopropane-1R-carboxylate. This will be called process β'.

In this process, the basic agent is preferably selected from the group consisting of ammonium hydroxide, n-butylamine, triethylamine, diethylamine, pyrrolidine, morpholine, piperidine, tetrabutyl ammonium hydroxide, Amberlite LA$_2$ and a catalytic amount of a strong base selected from the group consisting of sodium hydroxide, potassium hydroxide, alkali metal alcoholates, alkali metal amides and alkali metal hydrides in a solvent selected from the group consisting of acetone, benzene, dioxane, tetrahydrofuran, dimethylformamide and dimethylsulfoxide and mixtures thereof.

Among the chiral (A) acids of the cyclopropane carboxylic type, an other of the preferred acids is 2,2-dimethyl-3R-(2,2-dichlorovinyl)-cyclopropane-1R-carboxylic acid or 1R cis 2,2-dimethyl-3-(2,2-dichlorovinyl)-cyclopropane-carboxylic acid.

The invention also has as its object a process according to process α characterized by reacting an ester of 2,2-dimethyl-3R-(2,2-dichlorovinyl)-cyclopropane-1R-carboxylic acid and optically active (R) or (S) isomer of α-cyano-3-phenoxybenzyl alcohol or a mixture of the (R) and (S) isomers in non-equimolar proportions with a base selected from the group consisting of ammonium hydroxide, secondary and tertiary amines and a catalytic amount of a strong base in a solvent or mixture of solvents in which the starting ester is soluble and the esters of the racemic alcohol are soluble and isolating from the reaction solution the ester of 2,2-dimethyl-3R-(2,2-dichlorovinyl)-cyclopropane-1R-carboxylic acid and (R,S) α-cyano-3-phenoxybenzyl alcohol.

This procedure designated as process $\alpha_1$ is advantageously effected in the presence of a basic agent selected from the group consisting of ammonium hydroxide, triethylamine, diethylamine, pyrrolidine, morpholine, piperidine and a catalytic amount of a strong base selected from the group consisting of sodium hydroxide, potassium hydroxide, alkali metal alcoholates, alkali metal amides and alkali metal hydrides.

The said transformation by process $\alpha_1$ is preferably effected in at least one solvent selected from the group consisting of acetone, benzene, dioxane, tetrahydrofuran, dimethylformamide, dimethylsulfoxide and mixtures of the said solvents.

The invention has particularly as its object a process according to process $\alpha_1$, for the transformation of (R) α-cyano-3-phenoxybenzyl 2,2-dimethyl-3R-(2,2-dichlorovinyl)-cyclopropane-1R-carboxylate into (R,S) α-cyano-3-phenoxybenzyl 2,2-dimethyl-3R-(2,2-dichlorovinyl)-cyclopropane-1R-carboxylate comprising reacting the ester of the (R) alcohol with a base selected from the group consisting of ammonium hydroxide, secondary and tertiary amines and a catalytic amount of a strong base in a solvent selected from the group consisting of acetone, benzene, dioxane, tetrahydrofuran, dimethylformamide, dimethylsulfoxide and mixtures thereof and recovering the ester of the racemic alcohol from the reaction solution.

For this process designated as $\beta_1$, the transformation is preferably effected in the presence of triethylamine in dioxane and the ester of the racemic alcohol is recovered from the reaction solution by distillation to dryness.

The invention also is directed to the process according to process $\alpha_1$, wherein a mixture of (R) and (S) α-cyano-3-phenoxybenzyl 2,2-dimethyl-3R-(2,2-dichlorovinyl)-cyclopropane-1R-carboxylates in non-equimolecular proportions is transformed into (R,S) α-cyano-3-phenoxybenzyl 2,2-dimethyl-3R-(2,2-dichlorovinyl)-cyclopropane-1R-carboxylate by reacting the starting mixture of esters with a base selected from the group consisting of ammonium hydroxide, secondary and tertiary amines and a catalytic amount of a strong base in a solvent selected from the group consisting of acetone, benzene, dioxane, tetrahydrofuran, dimethylformamide, dimethylsulfoxide and mixtures thereof and isolating from the reaction solution the ester of the racemic alcohol.

For this process designated as $\gamma_1$, the transformation is advantageously effected in the presence of triethylamine in dioxane and the ester of the racemic alcohol is recovered from the reaction solution by distillation to dryness.

The invention equally has for its object the process according to process $\alpha_1$, wherein the starting ester is (S) α-cyano-3-phenoxybenzyl 2,2-dimethyl-3R-(2,2-dichlorovinyl)-cyclopropane-1R-carboxylate.

This process designated as $\delta_1$, is advantageously effected in the presence of triethylamine in dioxane.

The invention has also as object a process according to process $\alpha'$, comprising reacting an ester of 2,2-dimethyl-3R-(2,2-dichlorovinyl)-cyclopropane-1R-carboxylic acid and an optically active (R) or (S) isomer or a non-equimolecular mixture of (R) and (S) isomers of α-cyano-3-phenoxybenzyl alcohol with a basic agent selected from the group consisting of ammonium hydroxide, primary, secondary and tertiary amines, quaternary ammonium compounds, high molecular weight liquid amines and a catalytic amount of a strong base in a solvent or mixture of solvents in which the starting esters are soluble and which the ester of the racemic alcohol is soluble and then isolating from the reaction solution the (R,S) α-cyano-3-phenoxybenzyl 2,2-dimethyl-3R-(2,2-dichlorovinyl)-cyclopropane-1R-carboxylate.

This process designated as $\alpha_1'$, is preferably effected in the presence of a basic agent selected from the group consisting of ammonium hydroxide, n-butylamine, triethylamine, diethylamine, pyrrolidine, morpholine, piperidine, tetrabutylammonium hydroxide, Amberlite LA$_2$ and a catalytic amount of a strong base selected from the group consisting of sodium hydroxide, potassium hydroxide, alkali metal alcoholates, alkali metal amides and alkali metal hydrides.

The transformation of process $\alpha_1'$, is preferably effected in a solvent selected from the group consisting of acetone, benzene, dioxane, tetrahydrofuran, dimethylformamide, dimethylsulfoxide and mixtures thereof.

The mechanism of the reaction may be schematized in the following manner:

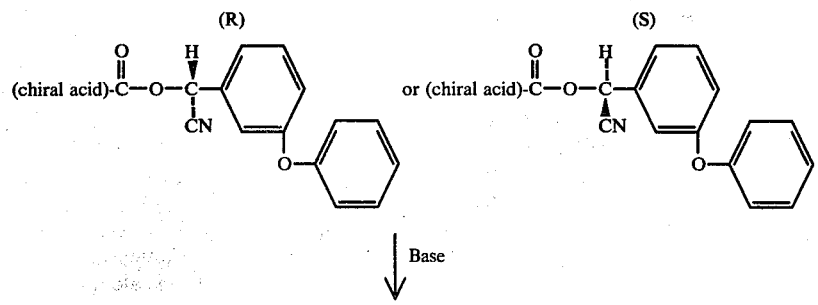

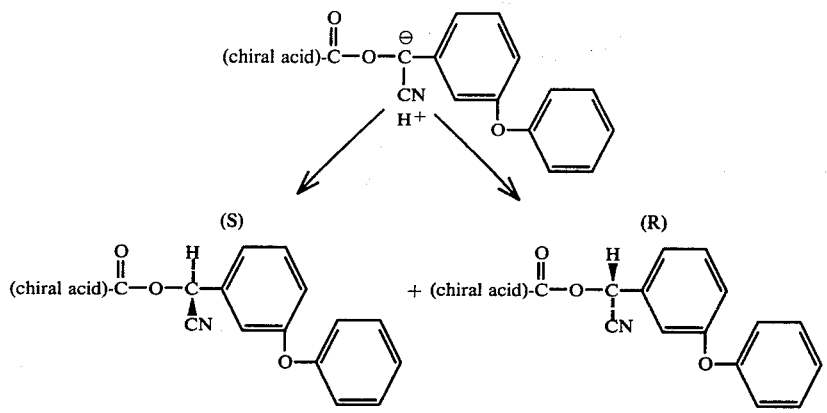

By the action of a base of suitable force as indicated above, the ester of the chiral acid and the optically active (R) or (S) isomer of the alcohol produces a α-cyanocarbanion which leads to the racemization of the corresponding carbon atom. The subsequent protonation in the solvent or mixture of solvents assuring the solubility of the various reactants leads to the formation of equimolecular proportions of the 2-diastereoisomers [ester of the (S) alcohol and ester of the (R) alcohol] that is to say, after isolation from the reaction media, to the formation of the ester of the racemic alcohol.

This theoretical explanation is merely an attempt to explain the results observed and is not intended to limit the invention in any fashion.

The transformation according to the invention of an ester of an optically active isomer of α-cyano-3-phenoxybenzyl alcohol into an ester of the racemic alcohol is effected at room temperature with quantitive yields and presents a very unexpected result and in as is so far as known does not have a known equivalent in the prior art.

The process of the invention is particularly interesting when the chiral acids used are the optically active cyclopropane carboxylic acids of the 1R,3R (or 1R, cis) or the 1R,3S (1R, trans) structure of the formula

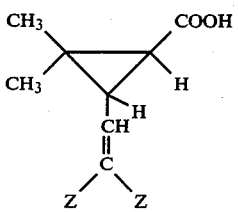

wherein Z is bromine or chlorine.

In effect for the last few years, insecticidal compounds with an exceptionally high activity have been prepared by esterifying the above chiral acids with α-cyano-3-phenoxybenzyl alcohol.

It has been established that in a general way the esters of the above chiral acids and the (S) α-cyano-3-phenoxybenzyl alcohol possess a much greater insecticidal activity than the corresponding esters of the (R,S) racemic alcohol or the (R) optical isomer of the alcohol. The α-cyano-3-phenoxybenzyl alcohol is obtained synthetically in a racemic form and the fragility of the molecule does not permit a stereoselective preparation of the enantiomeres nor the resolution of the racemic alcohol.

To obtain esters of the alcohol of the (S) configuration, the only procedure known to now consisted of effecting a separation of an ester of the (R) form and an ester of the (S) form of the alcohol by selective insolubilization of the last in a suitable solvent which leads to yields of esters of the (S) alcohol less than 50% with respect to the ester of the racemic alcohol used.

The ester of the (R) alcohol or mixtures of esters of the (R) and (S) alcohols, rich in the ester of the (R) alcohol arising from the preparation of the ester of the (S) alcohol thus appear to be not very interesting.

By the process of the invention, it is possible to transform the esters of (R) α-cyano-3-phenoxybenzyl alcohol or mixtures of esters of (R) α-cyano-3-phenoxybenzyl alcohol and (S) α-cyano-3-phenoxybenzyl alcohol containing more than 50% by weight of ester of the (R) alcohol into esters of racemic (R,S) α-cyano-3-phenoxybenzyl alcohol.

The ester of the (S) alcohol thus formed in the course of the processes at the expense of the ester of the (R) alcohol is able then to be isolated again from the ester of the racemic alcohol by insolubilization in a solvent, it is true, with a mediocre yield, or, which is better, to be transformed with an almost quantitative yield into the ester of the (S) alcohol as described in copending application Ser. No. 789,774 filed on even data herewith.

The process of the present invention permits now a revaluation of the esters of the (R) alcohol which had appeared to be residues of little value coming from the preparation of esters of the (S) alcohol. The revaluation is particularly advantageous in the case of esters of 2,2-dimethyl-3R-(2,2-dibromovinyl)-cyclopropane-1R-carboxylic acid or 2,2-dimethyl-3R-(2,2-dichlorovinyl)-cyclopropane-1R-carboxylic acid. Moreover, the process of the invention in a single step, simple in its manipulations, uses a reduced volume of solvent, does not require recourse to expensive reactants and permits to obtain an almost quantitative yield of an ester of the racemic alcohol.

The process of the invention presents a more general application than that which consists of transforming into an ester of a racemic (R,S) alcohol, the esters of chiral A acids and the (R) alcohol or mixtures of the (R) alcohol and (S) alcohol containing more than 50% by weight of the ester of the (R) alcohol as that results from the theoretical explanation of the process given hereinbefore and from the experimental results furnished hereafter. One can, in effect, by the process of the invention transform the esters of the (A) acid and the (S) alcohol as well as the mixtures of ester of the (R)

alcohol and the (S) alcohol containing more than 50% by weight of the ester of the (S) alcohol into an ester of the racemic alcohol.

In the following examples there are described several preferred embodiments to illustrate the invention. However, it is to be understood that the invention is not intended to be limited to the specific embodiments.

EXAMPLE 1

0.16 g of triethylamine were added to a solution of 1 g of (R) α-cyano-3-phenoxybenzyl 2,2-dimethyl-3R-(2,2-dibromovinyl)-cyclopropane-1R-carboxylate with a specific rotation of $[\alpha]_D = -30.5°$ (c=1% in benzene) and $[\alpha]_D = -25.5°$ (c=1% in chloroform) in 2.5 ml of acetone and the mixture was stirred for 15 hours at 20° C. The mixture was evaporated to dryness under reduced pressure to obtain 1 g of (R,S) α-cyano-3-phenoxybenzyl 2,2-dimethyl-3R-(2,2-dibromovinyl)-cyclopropane-1R-carboxylate which was chromatographed over silica gel. Elution with an 8-2 petroleum ether (b.p.=35°–70° C.)-isopropyl ether yielded two equal spots, one with an Rf=0.7 corresponding to the ester of the R alcohol and one with an Rf=0.64 corresponding to the ester of the S alcohol.

EXAMPLE 2

Using the procedure of Example 1 except that the acetone was replaced by benzene, the same ester of the racemic alcohol in the same quality of Example 1 was obtained.

EXAMPLE 3

Using the procedure of Example 1 except that the acetone was replaced by dioxane, the same ester of the racemic alcohol in the same amounts of Example 1 were obtained.

EXAMPLE 4

Using the procedure of Example 1 except that the acetone was replaced by tetrahydrofuran, the same ester of the racemic alcohol in the same amounts of Example 1 were obtained.

EXAMPLE 5

0.16 g of triethylamine was added to a solution of 1 g of (R) α-cyano-3-phenoxybenzyl 2,2-dimethyl-3R-(2,2-dibromovinyl)-cyclopropane-1R-carboxylate in 2.5 ml of dimethylformamide and the mixture was stirred at 20° C. for 15 hours. Water was added to the mixture and the mixture was extracted with methylene chloride. The organic phase was washed with water, dried and concentrated to dryness to obtain 1 g of (R,S) α-cyano-3- phenoxybenzyl 2,2-dimethyl-3R-(2,2-dibromovinyl)-cyclopropane-1R-carboxylate with a specific rotation of $[\alpha]_D^{20} = +13.5°$ (c=1% in benzene) and had the same chromatographic results as in Example 1 with the same spots with the same Rf.

EXAMPLE 6

Using the procedure of Example 5 except that dimethylformamide was replaced by dimethylsulfoxide, the same ester of the racemic alcohol was obtained of the same quality as Example 5.

EXAMPLE 7

Using the procedure of Example 1 with acetone except that the 0.16 g of triethylamine was replaced by 0.14 g of morpholine, the same ester of the racemic alcohol was obtained in the same yield and same quality as in Example 1.

EXAMPLE 8

Using the procedure of Example 2 with benzene except that the 0.16 g of triethylamine was replaced with 0.135 g of pyridine, the same ester of the racemic alcohol was obtained in the same yield with the same quality as in Example 1.

EXAMPLE 9

Using the procedure of Example 2 with benzene except that the 0.16 g of triethylamine was replaced with 0.11 g of pyrrolidine, the same ester of the racemic alcohol was obtained in the same yield and in the same quality as in Example 1.

EXAMPLE 10

Using the procedure of Example 1 with acetone except that the 0.16 g of triethylamine was replaced with 0.15 ml of an aqueous 22°Be' ammonium hydroxide solution, the same ester of the racemic alcohol was obtained in the same yield and in the same quality as in Example 1.

EXAMPLE 11

Using the procedure of Example 3 with dioxane except that the 0.16 g of triethylamine was replaced with 0.008 g of sodium hydroxide, the same ester of the racemic alcohol was obtained in the same yield and the same quality as in Example 1.

EXAMPLE 12

Using the procedure of Example 4 with tetrahydrofuran except that the 0.16 g of triethylamine was replaced with 0.014 g of sodium ethylate, the same ester of the racemic alcohol was obtained in the same yield and with the same quality as in Example 1.

EXAMPLE 13

0.16 g of triethylamine was added to a solution of 1 g of (S) α-cyano-3-phenoxybenzyl 2,2-dimethyl-3R-(2,2-dibromovinyl)-cyclopropane-1R-carboxylate with a specific rotation of $[\alpha]_D^{20} = +60.5°$ (c=1% in benzene) and $[\alpha]_D^{20} = +25°$ (c=1% in chloroform) and a melting point of 100° C., in 2.5 ml of acetone and the mixture was stirred for 15 hours at 20° C. The mixture was then evaporated to dryness under reduced pressure to obtain 1 g of (R,S) α-cyano-3-phenoxybenzyl 2,2-dimethyl-3R-(2,2-dibromovinyl)-cyclopropane-1R-carboxylate with a specific rotation of $[\alpha]_D^{20} = +13.5°$ (c=1% in benzene). The latter was chromatographed over silica gel and elution with an 8-2 petroleum ether (b.p.=35°–75° C.)-isopropyl ether yielded two equal spots, one with an Rf=0.7 corresponding to the ester of the (R) alcohol and the other with an Rf=0.64 corresponding to the ester of the (S) alcohol with quality of the ester being the same as in Example 1.

EXAMPLE 14

Using the procedure of Example 2 with 1 g of the ester of the (S) alcohol, the same yield of the ester of the racemic alcohol was obtained as in Example 1.

EXAMPLE 15

Using the procedure of Example 3, the ester of the (S) alcohol was reacted to obtain the same ester of the racemic alcohol in the same quality as in Example 1.

EXAMPLE 16

Using the procedure of Example 4, the ester of the (S) alcohol was reacted to obtain the same ester of the racemic alcohol in the same quality as in Example 1.

EXAMPLE 17

0.16 g of triethylamine was added to a solution of 1 g of (S) α-cyano-3-phenoxybenzyl 2,2-dimethyl-3R-(2,2-dibromovinyl)-cyclopropane-1R-carboxylate in 2.5 ml of dimethylformamide and the mixture was stirred for 15 hours at 20° C. The mixture was added with water and the mixture was extracted with methylene chloride. The organic extracts were washed with water, dried and evaporated to dryness to obtain 1 g of (R,S) α-cyano-3-phenoxybenzyl 2,2-dimethyl-3R-(2,2-dibromovinyl)-cyclopropane-1R-carboxylate in the same quality as in Example 1.

EXAMPLE 18

Using the procedure of Example 6, 1 g of the ester of the (S) alcohol was reacted to obtain the same yield of the ester of the racemic alcohol in the same quality as in Example 1.

EXAMPLE 19

Using the procedure of Example 7, 1 g of the ester of the (S) alcohol was reacted to obtain the same yield of the ester of the racemic alcohol in the same quality as in Example 1.

EXAMPLE 20

Using the procedure of Example 8, 1 g of the ester of the (S) alcohol was reacted to obtain the same yield of the ester of the racemic alcohol in the same quality as in Example 1.

EXAMPLE 21

Using the procedure of Example 9, 1 g of the ester of the (S) alcohol was reacted to obtain the same yield of the ester of the racemic alcohol in the same quality as in Example 1.

EXAMPLE 22

Using the procedure of Example 10, 1 g of the ester of the (S) alcohol was reacted to obtain the same yield of the ester of the racemic alcohol in the same quality as in Example 1.

EXAMPLE 23

Using the procedure of Example 11, 1 g of the ester of the (S) alcohol was reacted to obtain the same yield of the ester of the racemic alcohol in the same quality as in Example 1.

EXAMPLE 24

(1) Preparation: A solution of 10 g of (R,S) α-cyano-3-phenoxybenzyl 2,2-dimethyl-3R-(2,2-dibromovinyl)-cyclopropane-1R-carboxylate with a specific rotation of $[\alpha]_D^{20} = +13.5°$ (c=1% in benzene) in 20 ml of methanol was stirred for 20 hours at 20° C. and the mixture was vacuum filtered. The recovered precipitate was washed and dried to obtain 4 g of (S) α-cyano-3-phenoxybenzyl 2,2-dimethyl-3R-(2,2-dibromovinyl)-cyclopropane-1R-carboxylate melting at 100° C. and having a specific rotation of $[\alpha]_D^{20} = +60.5°$ (c=1% in benzene) and $[\alpha]_D^{20} = +25°$ (c=1% in chloroform). The mother liquor were evaporated to dryness under reduced pressure to obtain 6 g of a mixture of 5 g of (R) α-cyano-3-phenoxybenzyl 2,2-dimethyl-3R-(2,2-dibromovinyl)-cyclopropane-1R-carboxylate and 1 g of (S) α-cyano-3-phenoxybenzyl 2,2-dimethyl-3R-(2,2-dibromovinyl)-cyclopropane-1R-carboxylate designated as mixture M.

(2) Mixture M was dissolved in 20 ml of benzene and 1 g of triethylamine was added thereto. The mixture was then stirred at 20° C. for 18 hours and was evaporated to dryness under reduced pressure to obtain 6 g of (R,S) α-cyano-3-phenoxybenzyl 2,2-dimethyl-3R-(2,2-dibromovinyl)-cyclopropane-1R-carboxylate in the same quality of Example 1. The product had a specific rotation of $[\alpha]_D^{20} = +13.5°$ (c=1% in benzene) and showed 2 equal spots by chromatography.

EXAMPLE 25

A mixture of the ester of the (R) and (S) alcohols was obtained as in Example 24 and the mixture was racemized as in Example 24 except that the 1 g of triethylamine was replaced with 0.9 g of pyrrolidine to obtain the esters of the racemic alcohol with same yield and quality as in Example 24.

EXAMPLE 26

0.13 g of triethylamine was added to a solution of 1 g of (R) α-cyano-3-phenoxybenzyl 2,2-dimethyl-3R-(2,2-dichlorovinyl)-cyclopropane-1R-carboxylate in 2.7 ml of dioxane and the solution was stirred for 15 hours at 20° C. The mixture was concentrated to dryness under reduced pressure to obtain 1 g of (R,S) α-cyano-3-phenoxybenzyl 2,2-dimethyl-3R-(2,2-dichlorovinyl)-cyclopropane-1R-carboxylate with a specific rotation of $[\alpha]_D^{20} = +16°$ (c=1% in benzene). The latter was chromatographed over silica gel and elution with an 8-2 petroleum ether (b.p.=35°–75° C.)-isopropyl ether mixture to obtain two equal spots, one with an Rf=0.68 corresponding to the ester of the (R) alcohol and one with an Rf=0.62 corresponding to the ester of the (S) alcohol.

EXAMPLE 27

Using the procedure of Example 26, 1 g of (S) α-cyano-3-phenoxybenzyl 2,2-dimethyl-3R-(2,2-dichlorovinyl)-cyclopropane-1R-carboxylate with a melting point of 60° C. and a specific rotation of $[\alpha]_D^{20} = +66°$ (c=1% in benzene) was reacted to obtain 1 g of (R,S) α-cyano-3-phenoxybenzyl 2,2-dimethyl-3R-(2,2-dichlorovinyl)-cyclopropane-1R-carboxylate of the same quality as that of Example 26.

EXAMPLE 28

(1) Preparation A solution of 20 g of (R,S) α-cyano-3-phenoxybenzyl 2,2-dimethyl-3R-(2,2-dichlorovinyl)-cyclopropane-1R-carboxylate with a specific rotation of $[\alpha]_D^{20} = +16.5°$ (c=1% in benzene) in 40 ml of methanol was stirred for 24 hours at 0°–5° C. and was then vacuum filtered. The recovered precipitate was washed and dried to obtain 5.6 g of (S) α-cyano-3-phenoxybenzyl 2,2-dimethyl-3R-(2,2-dichlorovinyl)-cyclopropane-1R-carboxylate melting at 60° C. and having a specific rotation of $[\alpha]_D^{20} = +66°$ (c=1% in benzene). The mother liquors were evaporated to dryness to obtain 14.4 g of a mixture $M^1$ of 10 g of (R) α-cyano-3-phenoxybenzyl 2,2-dimethyl-3R-(2,2-dibromovinyl)-cyclopropane-1R-carboxylate and 4.4 g of (S) α-cyano-3-phenoxybenzyl 2,2-dimethyl-3R-(2,2-dichlorovinyl)-cyclopropane-1R-carboxylate.

(2) The mixture M¹ was dissolved in 40 ml of dioxane and 2 g of triethylamine were added thereto after which the mixture was stirred for 20 hours at 20° C. The mixture was concentrated to dryness under reduced pressure to obtain 14.4 g of (R,S) α-cyano-3-phenoxybenzyl 2,2-dimethyl-3R-(2,2-dichlorovinyl)-cyclopropane-1R-carboxylate with a specific rotation of $[\alpha]_D^{20} = +16°$ (c=1% in benzene). The product was chromatographed over silica gel and elution with an 8-2 petroleum ether (b.p.=35°-75° C.)—isopropyl ether mixture yielded 2 equal spots, one with an Rf=0.68 corresponding to the ester of the (R) alcohol and the other with an Rf=0.62 corresponding to the ester of the (S) alcohol.

EXAMPLE 29

0.785 ml of n-butylamine was added to a solution of 10 g of (S) α-cyano-3-phenoxybenzyl 1R, cis-2,2-dimethyl-3-(2,2-dibromovinyl)-cyclopropane-1-carboxylate with a specific rotation of $[\alpha]_D^{20} = +58° \pm 1$ (c=4% into toluene) in 25 ml of benzene and the mixture was stirred for 72 hours at 20° C. The mixture was evaporated to dryness under reduced pressure to obtain 10 g of a residue which was chromatographed over silica gel. Elution with benzene yielded 9.1 g of (R,S) α-cyano-3-phenoxybenzyl 1R, cis 2,2-dimethyl-3-(2,2-dibromovinyl)-cyclopropane-1-carboxylate with a specific rotation of $[\alpha]_D^{20} = +7.5°$ (c=4% in toluene).

EXAMPLE 30

1 g of tetrabutylammonium hydroxide was added to a solution of 10 g of (S) α-cyano-3-phenoxybenzyl 1R, cis 2,2-dimethyl-3-(2,2-dibromovinyl)-cyclopropane-1-carboxylate with a specific rotation of $[\alpha]_D^{20} = +58° \pm 1$ (c=4% in toluene) in 250 ml of toluene and the mixture was stirred for 24 hours and was then concentrated to dryness under reduced pressure to obtain 10.2 g of a residue. The latter was chromatographed over silica gel and was eluted with toluene to obtain 8.9 g of (R,S) α-cyano-3-phenoxybenzyl 1R, cis 2,2-dimethyl-3-(2,2-dibromovinyl)-cyclopropane-1-carboxylate with a specific rotation of $[\alpha]_D^{20} = +7.5°$ (c=4% in toluene).

EXAMPLE 31

10 g of Amberlite LA₂ were added to a solution of 10 g of (S) α-cyano-3-phenoxybenzyl 1R, cis 2,2-dimethyl-3-(2,2-dibromovinyl)-cyclopropane-1-carboxylate with a specific rotation of $[\alpha]_D^{20} = +58° \pm 1°$ (c=4% in toluene) in 30 ml of benzene and the mixture was stirred for 72 hours and was then concentrated to dryness under reduced pressure. The residue was chromatographed over silica gel and was eluted with toluene to obtain 9 g of (R,S) α-cyano-3-phenoxybenzyl 1R, cis 2,2-dimethyl-3-(2,2-dibromovinyl)-cyclopropane-1R-carboxylate with a specific rotation of $[\alpha]_D^{20} = +7.5°$ (c=4% in toluene).

Various modifications of the process of the invention may be made without departing from the spirit or scope thereof and it should be understood that the invention is intended to be limited only as defined in the appended claims.

We claim:

1. A process for the preparation of an ester of chiral (A) acid with a racemic (R,S) α-cyano-3-phenoxybenzyl alcohol (B) comprising reacting an ester of chiral (A) acid with α-cyano-3-phenoxybenzyl alcohol of the formula

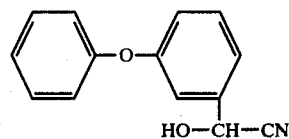

in its optically active (R) form or (S) form or a mixture of esters of said (R) alcohol and (S) alcohol in non-equimolecular proportions with a base selected from the group consisting of ammonia, primary, secondary and tertiary amines, quaternary ammonium compounds, liquid amines of high molecular weight and a catalytic amount of a strong base in at least one solvent for the starting esters and in which the ester of racemic alcohol is soluble and recovering from the resulting solution the ester of chiral (A) acid with racemic (R,S) alcohol.

2. The process of claim 1 wherein the base is selected from the group consisting of ammonium hydroxide, secondary and tertiary amines and a catalytic amount of a strong base.

3. The process of claim 2 wherein the chiral (A) acid possesses an asymetrical carbon atom.

4. The process of claim 2 wherein the chiral (A) acid possesses two asymetrical carbon atoms.

5. The process of claim 2 wherein the chiral (A) acid is a cyclopropane carboxylic acid having 2 asymetrical carbon atoms in the ring.

6. The process of claim 2 wherein the chiral (A) acid is a cis or trans optically active cyclopropane carboxylic acid of the formula

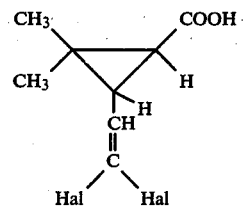

wherein Hal is bromine or chlorine.

7. The process of claim 2 wherein the chiral (A) acid is 2,2-dimethyl-3R-(2,2-dibromovinyl)-cyclopropane-1R-carboxylic acid.

8. The process of claim 2 wherein the chiral (A) acid is 2,2-dimethyl-3R-(2,2-dichlorovinyl)-cyclopropane-1R-carboxylic acid.

9. The process of claim 2 wherein the base is selected from the group consisting of ammonium hydroxide, triethylamine, diethylamine, pyrrolidine, morpholine, piperidine and a catalytic amount of a strong base selected from the group consisting of sodium hydroxide, potassium hydroxide, alkali metal alcoholates, alkali metal amides and alkali metal hydrides.

10. A process of claim 2 wherein the organic solvent is selected from the group consisting of ketones, aromatic monocyclic hydrocarbons, ether oxides, dimethylformamide, dimethylsulfoxide and mixtures thereof.

11. The process of claim 10 wherein the solvent is selected from the group consisting of acetone, benzene, dioxane, tetrahydrofuran, dimethylformamide, dimethylsulfoxide and mixtures thereof.

12. The process of claim 7 wherein the base is selected from the group consisting of ammonium hydroxide, triethylamine, diethylamine, pyrrolidine, morpholine, piperidine and a catalytic amount of a strong base selected from the group consisting of sodium hydroxide, potassium hydroxide, alkali metal alcoholates, alkali metal amides and alkali metal hydrides.

13. The process of claim 7 wherein the solvent is selected from the group consisting of acetone, benzene, dioxane, tetrahydrofuran, dimethylformamide, dimethylsulfoxide and mixtures thereof.

14. The process of claim 2 wherein the starting ester is (R) α-cyano-3-phenoxybenzyl-2,2-dimethyl-3R-(dibromovinyl)-cyclopropane-1R-carboxylate and the solvent is selected from the group consisting of acetone, benzene, dioxane, tetrahydrofuran, dimethylformamide, dimethylsulfoxide and mixtures thereof.

15. The process of claim 2 wherein the starting ester is a mixture of the (R) and (S) α-cyano-3-phenoxybenzyl 2,2-dimethyl-3R-(2,2-dibromovinyl)-cyclopropane-1R-carboxylates in non-equimolecular proportions and the solvent is selected from the group consisting of acetone, benzene, dioxane, tetrahydrofuran, dimethylformamide, dimethylsulfoxide and mixtures thereof.

16. The process of claim 2 wherein the starting material is (S) α-cyano-3-phenoxybenzyl 2,2-dimethyl-3R-(2,2-dibromovinyl)-1R-carboxylate.

17. The process of claim 8 wherein the base is selected from the group consisting of ammonium hydroxide, triethylamine, diethylamine, pyrrolidine, morpholine, piperidine and a catalytic amount of a strong base selected from the group consisting of sodium hydroxide, potassium hydroxide, alkali metal alcoholates, alkali metal amides and alkali metal hydrides.

18. The process of claim 8 wherein the solvent is selected from the group consisting of acetone, benzene, dioxane, tetrahydrofuran, dimethylformamide, dimethylsulfoxide and mixtures thereof.

19. The process of claim 2 wherein the starting ester is (R) α-cyano-3-phenoxybenzyl 2,2-dimethyl-3R-(dichlorovinyl)-cyclopropane-1R-carboxylate and the solvent is selected from the group consisting of acetone, benzene, dioxane, tetrahydrofuran, dimethylformamide, dimethylsulfoxide and mixtures thereof.

20. The process of claim 2 wherein the starting ester is a mixture of the (R) and (S) α-cyano-3-phenoxybenzyl 2,2-dimethyl-3R-(2,2-dichlorovinyl)-cyclopropane-1R-carboxylates in non-equimolecular proportions and the solvent is selected from the group consisting of acetone, benzene, dioxane, tetrahydrofuran, dimethylformamide, dimethylsulfoxide and mixtures thereof.

21. The process of claim 12 wherein the starting material is (S) α-cyano-3-phenoxybenzyl 2,2-dimethyl-3R-(2,2-dichlorovinyl)-cyclopropane-1R-carboxylate.

22. The process of claim 1 wherein the chiral (A) acid is selected from acids possessing one asymetrical carbon atoms and acids possessing 2 asymetrical carbon atoms and the base is selected from the group consisting of primary amine, quaternary ammonium compounds and high molecular weight liquid amines.

23. The process of claim 1 wherein the chiral (A) acid is a cis or trans optically active cyclopropane carboxylic acid of the formula

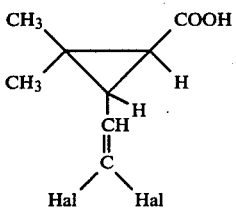

wherein Hal is bromine or chlorine and the base is selected from the group consisting of primary amines, quaternary ammonium compounds and high molecular weight amines.

24. The process of claim 1 wherein the chiral (A) acid is selected from the group consisting of 2,2-dimethyl-3R-(2,2-dibromovinyl)-cyclopropane-1R-carboxylic acid and 2,2-dimethyl-3R-(2,2-dichlorovinyl)-cyclopropane-1R-carboxylic acid.

25. The process of claim 24, wherein the base is selected from the group consisting of primary amines, quaternary ammonium compounds and high molecular weight amines.

* * * * *